(12) United States Patent
Kim et al.

(10) Patent No.: US 8,546,361 B2
(45) Date of Patent: Oct. 1, 2013

(54) PSEUDOLIPID COMPLEX MIXTURE AND A SKIN EXTERNAL APPLICATION COMPOSITION CONTAINING SAME

(75) Inventors: Do Hoon Kim, Seoul (KR); Eun Jung An, Paju-si (KR); Jae Sung Hwang, Seoul (KR); Hong Ju Shin, Seongnam-si (KR); Won Seok Park, Seoul (KR); Chang Geun Yi, Yongin-si (KR); Jong Hee Park, Yongin-si (KR); Jeong Hwan Kim, Paju-si (KR)

(73) Assignee: Amorepacific Corporation, Seoul (KR)

( * ) Notice: Subject to any disclaimer, the term of this patent is extended or adjusted under 35 U.S.C. 154(b) by 132 days.

(21) Appl. No.: 13/003,519

(22) PCT Filed: Sep. 2, 2008

(86) PCT No.: PCT/KR2008/005144
§ 371 (c)(1),
(2), (4) Date: Jan. 10, 2011

(87) PCT Pub. No.: WO2010/005144
PCT Pub. Date: Jan. 14, 2010

(65) Prior Publication Data
US 2011/0118222 A1    May 19, 2011

(30) Foreign Application Priority Data

Jul. 11, 2008    (KR) .................. 10-2008-0067676

(51) Int. Cl.
| | | |
|---|---|---|
| A01N 45/00 | (2006.01) | |
| A01N 37/00 | (2006.01) | |
| A61K 31/56 | (2006.01) | |
| A61K 31/20 | (2006.01) | |

(52) U.S. Cl.
USPC .......................................... 514/171; 514/558

(58) Field of Classification Search
None
See application file for complete search history.

(56) References Cited

U.S. PATENT DOCUMENTS

| | | |
|---|---|---|
| 5,939,077 A | 8/1999 | Saint-Leger et al. |
| 2004/0219177 A1 | 11/2004 | Jacobs |

FOREIGN PATENT DOCUMENTS

| | | |
|---|---|---|
| JP | 09-067224 A | 3/1997 |
| JP | 10-226674 A | 8/1998 |
| JP | 11-049634 A | 2/1999 |
| JP | 2001-270816 A | 10/2001 |
| JP | 2001-316384 A | 11/2001 |
| JP | 2005-002018 A | 1/2005 |
| JP | 2006-290751 A | 10/2006 |
| JP | 2008-520630 A | 6/2008 |
| WO | 94/00127 A1 | 1/1994 |
| WO | 03/072540 A1 | 9/2003 |
| WO | 2006/053912 A1 | 5/2006 |

OTHER PUBLICATIONS

Ishikawa et al. "XP002679093" retrieved from STN Database accession No. 1997:329075 on Jul. 2, 2012.
Mizushima et al., "Thermotropic Behavior of Stratum Corneum Lipids Containing a Pseudo-Ceramide," Lipids, 1995, vol. 30, No. 4, pp. 327-332.
Mizushima et al., "Phase Behavior of Artificial Stratum Corneum Lipids Containing Pseudo-Ceramide: a Study of the Function of Cholesterol," 1996, Journal of Lipid Research, vol. 37, No. 2, pp. 361-367.
Park et al., "The Characterization of Molecular Organization of Mutilamellar Emulsions Containing Pseudoceramide and Type III Synthetic Ceramide," the Society for Investigative Dermatology, Inc., 2003, vol. 121, No. 4, pp. 794-801.
Park et al., "Improvement of Skin Barrier Function Using Lipid Mixture," SÖFW-Journal, 2001, vol. 127, No. 9, pp. 16-18.
Lieckfeldt et al., "Diffusivity and Structural Polymorphism in Some Model Stratum Corneum Lipid Systems," Biochimica et Biophysica Acta, 1993, vol. 1150, No. 2, pp. 182-188.
European Patent Office, European Office Action issued in corresponding EP application No. 08811637.1, dated Jul. 16, 2012.
Mizushima H, et al., J. Cooloid. Interface Sci., Nov. 1, 1997:195(1): 156-63 (Abstract).

*Primary Examiner* — Anna Pagonakis
(74) *Attorney, Agent, or Firm* — Sughrue Mion, PLLC

(57) ABSTRACT

Provided is a pseudolipid complex mixture comprising a pseudoceramide and a stearic acid and an external skin application composition comprising the same. The complex mixture has improved phase stability and a structure similar to that of the stratum corneum which can retain water and other beneficial materials, and accordingly the composition comprising the same can be used as an external skin application composition having improved moisturization and barrier repair capabilities.

2 Claims, 6 Drawing Sheets

(a) PC104 50%+SA 50%+Chol 0%
(b) PC104 45%+SA 45%+Chol 10%
(c) PC104 40%+SA 40%+Chol 20%
(d) PC104 35%+SA 35%+Chol 30%
(e) PC104 30%+SA 30%+Chol 40%
(f) PC104 25%+SA 25%+Chol 50%
(g) pc104 0%+SA 0%+chol 100%

PSEUDOLIPID COMPLEX MIXTURE AND A SKIN EXTERNAL APPLICATION COMPOSITION CONTAINING SAME

CROSS REFERENCE TO RELATED APPLICATIONS

This application is a National Stage of International Application No. PCT/KR2008/005144, filed on Sep. 2, 2008, which claims priority from Korean Patent Application No. 10-2008-0067676 filed on Jul. 11, 2008, the contents of all of which are incorporated herein by reference in their entirety.

FIELD OF THE INVENTION

The present invention relates to a pseudolipid complex mixture, and to an external skin application composition containing the same having improved epidermal moisturization and skin barrier repair capabilities.

BACKGROUND OF THE INVENTION

The surface of human epidermis is composed of corneocytes, flat-shaped keratin proteins formed from keratinocytes which are the major component of the epidermis generated from the stratum basale by cell proliferation. The corneocytes function to maintain the smoothness and elasticity of the skin by binding to the double-chained lamellar structure of ceramides which are abundantly present in the stratum corneum. A ceramide is a sphingolipid composed of sphingosine and a fatty acid linked to sphingosine or phytosphingosine. A family of ceramides, which make up about 40% or more of the lipids present in cornified cells, is known to be essential in controlling the structural organization and functions of the stratum corneum, and they also have other vital physiological properties.

Ceramides protect the skin from internal/external stresses, e.g., by removing disrupted cells, and they become depleted with advancing age. As a consequence, water loss, exposure to the external stimuli such as ultraviolet or chemicals, and exfoliation of cornified cells take place, which causes the skin to become dry, cracked and fissured.

Such symptoms may be partially ameliorated by external application of ceramides. However, if a large amount of ceramides are used in a cosmetic formulation, instability and gelation of the formulation may occur.

The present inventors have unexpectedly found that a complex mixture composed of a pseudoceramide, a cholesterol, and a stearic acid is stable and has an improved water retention capacity, and that a composition containing the same has improved capabilities for skin moisturization and restoration of the interest ceramide functions.

SUMMARY OF THE INVENTION

Accordingly, it is an object of the present invention to provide a pseudolipid complex mixture having improved phase stability and a structure similar to that of the stratum corneum which can retain a large amount of water and other beneficial materials.

It is another object of the present invention to provide an external application composition comprising said complex mixture having improved cutaneous moisturization and barrier repair capabilities.

In accordance with an aspect of the present invention, there is provided a pseudolipid complex mixture comprising a pseudoceramide and a stearic acid.

In the complex mixture, the amounts of the pseudoceramide and stearic acid may be each 10 to 90% by weight based on the total weight of the complex mixture.

The complex mixture of the present invention may further comprise a cholesterol. Preferably, the amounts of the pseudoceramide, cholesterol, and stearic acid may be 10 to 80% by weight, 0.0001 to 30% by weight, and 10 to 80% by weight, respectively.

In accordance with another aspect of the present invention, there is provided an external skin application composition comprising the pseudolipid complex mixture as disclosed above.

In the external skin application composition, said complex mixture may be used in an amount of 0.01 to 40% by weight based on the total weight of the composition.

The external skin application composition may be a cosmetic composition or a pharmaceutical composition.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
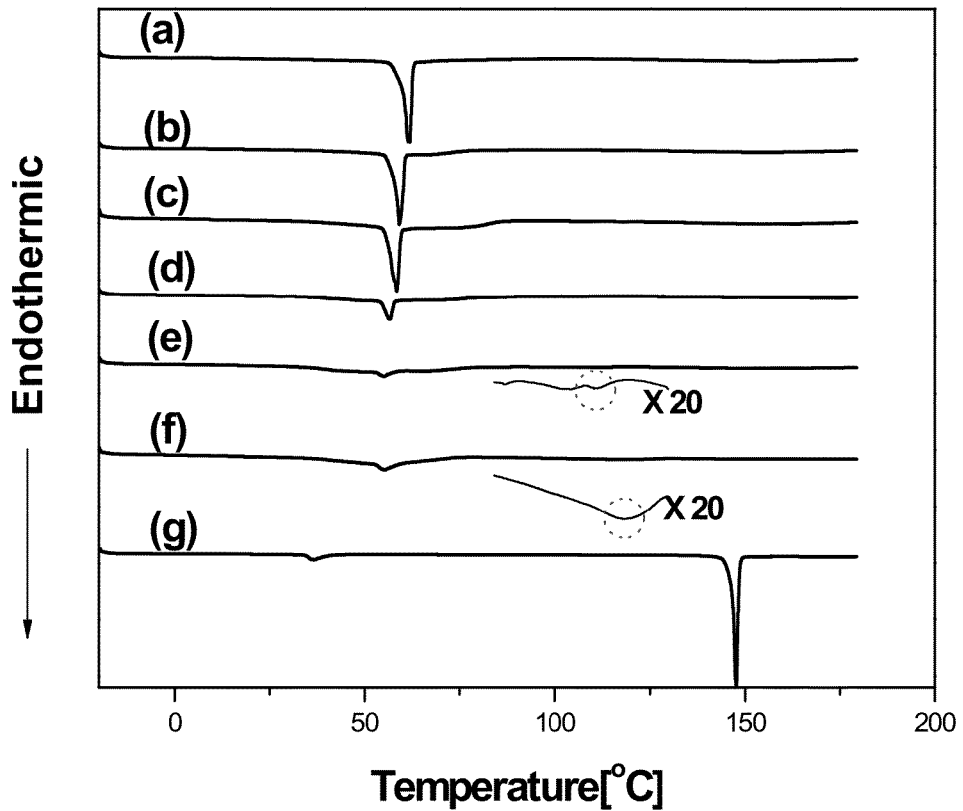
FIG. 1: phase behaviors of a mixture composed of a pseudoceramide, a cholesterol, and a stearic acid, observed by DSC (differential scanning calorimetry) (PC104: pseudoceramide, SA: stearic acid, Chol: cholesterol)
Figure 2:
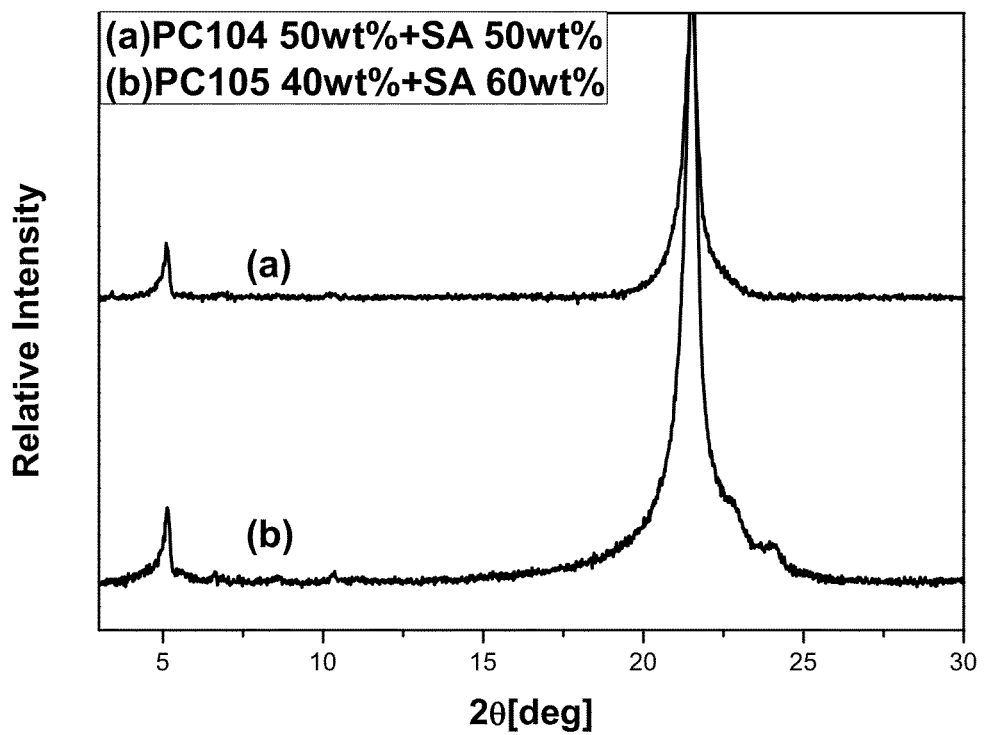
FIG. 2: X-ray diffraction analysis showing that a mixture of a pseudoceramide and a stearic acid has a lamellae structure similar to that of the stratum corneum (PC: pseudoceramide, SA: stearic acid)
Figure 3:
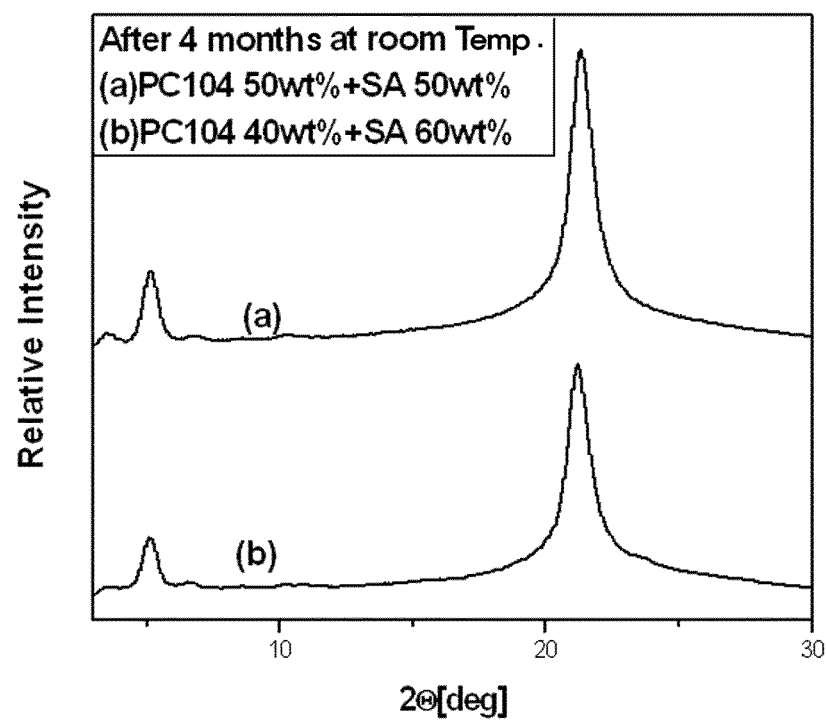
FIG. 3: X-ray diffraction analysis showing that a mixture of a pseudoceramide and a stearic acid maintains a lamellae structure even after 4 month (PC: pseudoceramide, SA: stearic acid)
Figure 4:
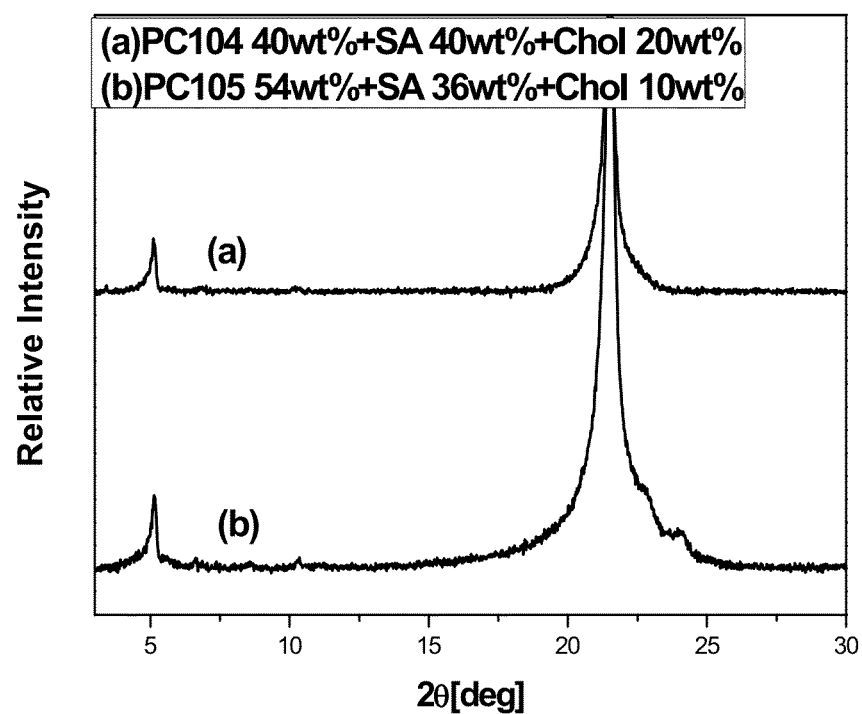
FIG. 4: X-ray diffraction analysis showing that a mixture of a pseudoceramide, a cholesterol, and a stearic acid has a lamellae structure similar to that of the stratum corneum (PC: pseudoceramide, SA: stearic acid, Chol: cholesterol)
Figure 5:
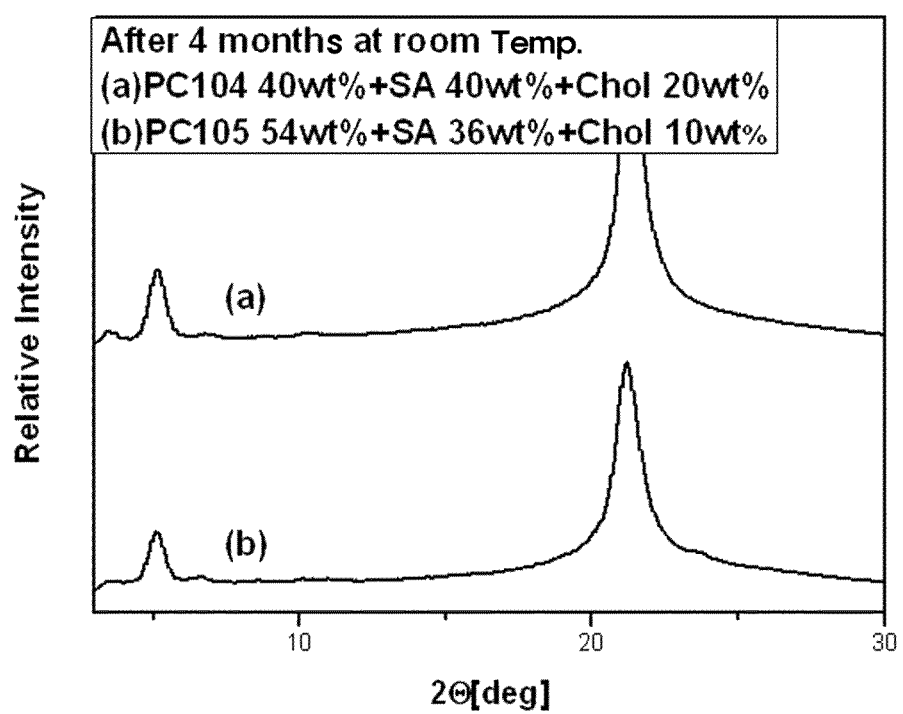
FIG. 5: X-ray diffraction analysis showing that a mixture of a pseudoceramide a cholesterol, and a stearic acid maintains a lamellae structure even after 4 month (PC: pseudoceramide, SA: stearic acid, Chol: cholesterol)

The present invention is described in detail hereinafter.

The present invention provides a pseudolipid complex mixture comprising a pseudoceramide and a stearic acid.

The pseudoceramide used herein is a synthetic material which is similar to a natural ceramide in terms of properties, e.g., skin protection and water retention capabilities.

Said pseudoceramide may be one of compounds represented by formulae (I) to (VI), but not limited thereto:

(I)

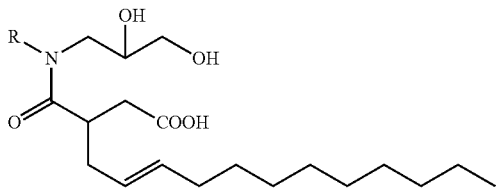

(wherein,

R is a saturated or unsaturated $C_9$-$C_{21}$ aliphatic chain moiety);

(II)

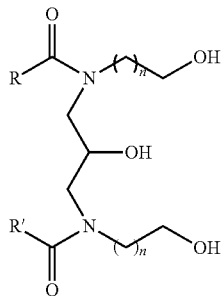

(wherein, n is 1 or 2; and

R and R' are each a saturated or unsaturated $C_9$-$C_{21}$ aliphatic chain moiety);

(III)

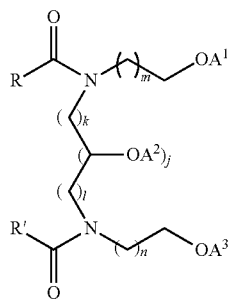

(wherein, m and n are each independently an integer of 1 to 3;

k and l are each independently 1 or 2;

j is 0 or 1;

R and R' are each independently a linear or branched, saturated or unsaturated $C_1$-$C_{31}$ hydrocarbon group having one or more hydroxyl substituents; and $A^1$, $A^2$ and $A^3$ are each independently hydrogen or one of following groups, with the proviso that A1, A2 and A3 are not simultaneously hydrogen.

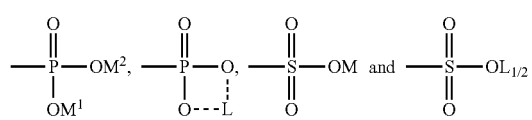

[wherein,

M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal.]);

(IV)

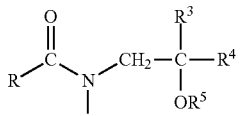

(wherein,

R and R' are each independently a linear or branched, saturated or unsaturated $C_{10}$-$C_{32}$ hydrocarbon group, optionally having one or more hydroxyl substituents;

$R^3$ and $R^4$ are each independently hydrogen, $C_1$-$C_4$ alkyl, or $C_1$-$C_4$ hydroxyl alkyl; and $R^5$ is -A or —$CH_2CH_2OA$, wherein A is one of following groups;

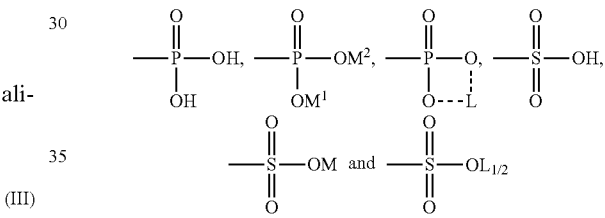

[wherein,

M, $M^1$ and $M^2$ are each independently selected from the group consisting of an alkali metal, a lysine moiety, an arginine moiety, a histidine moiety, triethylammonium, ammonium, polyquaternium-4, polyquaternium-6, polyquaternium-7, polyquaternium-10, polyquaternium-11, polyquaternium-16, lauryldimethylbenzylammoniumchloride and stearyldimethylbenzylammoniumchloride, and L is an alkali earth metal.]);

(V)

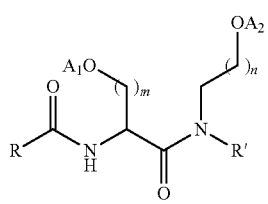

(Wherein, m and n are each independently an integer of 1 to 4;

R and R' are each independently a linear or branched, saturated or unsaturated $C_1$-$C_{31}$ hydrocarbon group, optionally having one or more hydroxyl substituents;

$A_1$ and $A_2$ are each independently hydrogen or one of following groups:

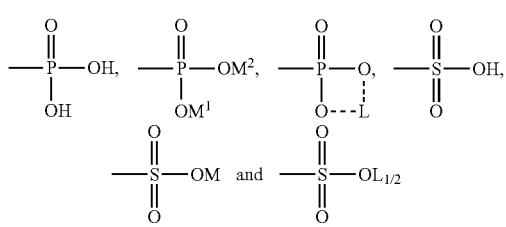

[wherein,
$M$, $M^1$ and $M^2$ are each independently an alkali metal or a nitrogen-containing organic base, and L is an alkali earth metal.]);

(VI)

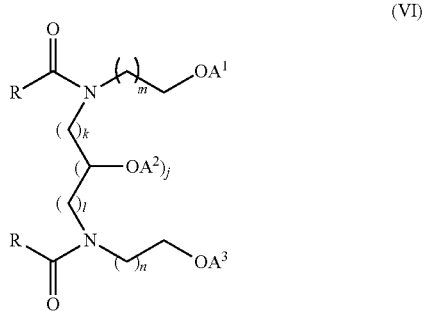

(Wherein,
m and n are each independently an integer of 1 to 3;
k and l are each independently 1 or 2;
j is 0 or 1; and
$A^1$, $A^2$ and $A^3$ are each independently hydrogen or one of following groups:

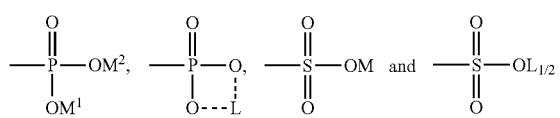

[wherein,
$M$, $M^1$ and $M^2$ are each independently an alkali metal or a nitrogen-containing organic base, and L is an alkali earth metal.];
R is a substituent of following structure:

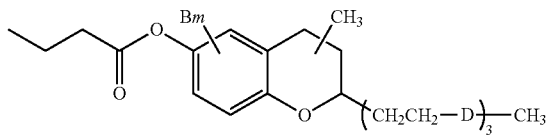

[wherein,
B is a methyl group in 5-, 7-, or 8-position of tocopherol; m is an integer of 1 to 3, and D is —CH$_2$(CH$_3$)—CH— or —CH(CH$_3$)=C—]).

The above-mentioned compounds of formulae (I) to (VI) have improved cutaneous moisturization and skin barrier repair capabilities, and are available from Amore Pacific Co. (Korea) under the trade names of ceramides PC104, PC102, PC107 etc.

In the complex mixture of the present invention, the ceramide may be used in an amount of about 10 to 90% by weight, preferably in an amount of 40 to 70% by weight, based on the total amount of the complex mixture. When used in said amount, the complex mixture of the present invention shows improved phase stability and water retention capacity. Thus, the complex mixture of the present invention is effective in moisturizing the skin and also repairing of the skin's barrier function.

The stearic acid used herein, one of fatty acids, may be used in an amount of about 10 to 90% by weight, preferably in an amount of 40 to 70% by weight, based on the total amount of the complex mixture of the present invention.

The complex mixture of the present invention may further comprise a cholesterol.

Cholesterols are one of the lipids components constituting the cellular membranes together with ceramides and fatty acids, and they play an important role in structural organization and functions of the stratum corneum. (Elias, P. M., Arch. Dermatol. Res., 270: 95-117 (1981)).

When the complex mixture of the present invention comprises a cholesterol, said pseudoceramide and stearic acid may be used in amounts of about 10 to 80% by weight, preferably in amounts of about 30 to 60% by weight, respectively, and the cholesterol may be used in an amount of about 0.0001 to 30% by weight, preferably in an amount of about 10 to 30% by weight.

In the complex mixture of the present invention, the ratio of the pseudoceramide, cholesterol, and stearic acid may be adjusted in accordance with the desired solubility, stability and water retention capacity of the ceramide. Generally, the pseudoceramide and stearic acid may be used in a weight ratio of 1:1, and the pseudoceramide and cholesterol, in a weight ratio of 1:0.5. These ratios are determined based on the observation of the phase behavior of the complex mixture, using differential scanning calorimetry, as shown in FIG. 1. In such a way that crystallization or phase separation does not occur, which the complex mixture maintain a lamellar structure similar to that of the stratum corneum.

The complex mixture of the present invention is capable of maintaining the lamellar structure as the X-ray diffraction analysis results show (see FIGS. 2, 3, 4 and 5).

Accordingly, the complex mixture of the present invention is capable of retaining insoluble materials (e.g., ceramide 3B etc.) in the double-layered lamellar structures.

Thus, the inventive complex mixture is biocompatible, and has improved water retention capacity, as well as good storage stability.

The present invention also provides an external skin application composition comprising said complex mixture, which comprises said complex mixture in an amount of about 0.01 to 40% by weight, preferably in an amount of about 0.01 to 15% by weight. The inventive composition exhibits improved storage stability, its moisturization and skin barrier repair functions being maintained over a long period of time.

The external skin application composition of the present invention may comprise vesicles or carriers commonly used for preparing cosmetics. The composition may be formulated into cosmetic compositions, for example, skin lotion, nourishing lotion, massage cream, nourishing cream, pack, gel or other adhesive type of cosmetics, but not limited thereto. Preferably, the composition may be formulated into an oil-in-water emulsion or solubilized gel which has phase stability.

The external skin application composition may be a pharmaceutical composition in which the complex mixture of the present invention is dispersed or dissolved in a pharmaceutically acceptable carrier, and examples are lotions, solutions, gels, creams, emollient creams, unguents, patches and sprays.

The pharmaceutical composition may be used for the treatment and prevention of, for example, atopic dermatitis, miliaria, erosion, frostbite, diaper rash, contact dermatitis, seborrheic dermatitis, lichen Vidal, nummular dermatitis, housewife's eczema, photosensitivity dermatitis, insect bites, pruritus cutaneous, prurigo, drug eruption, toxic erythema, psoriasis, parapsoriasis, Pustulosis palmoplantaris, lichen planus, lichen nitidus, pityriasis rubra pilaris, Gibert pityriasis rosea, erythroplakia, dermatitis exfoliativa, dicoid lupus erythematosus, systemic lupus erythematosus, pemphigus, bollous pemphigoid, dermatitis herpetiformis Duhring, alopecia greata, vitiligo vulgaris, sarcoidosis, cutaneous amyloidosys, keloids, hypertrophic scars, wounds, bed sores, cutaneous ulcers, alopecia, hair growth.

The external skin application composition of the present invention may also function as a base for the delivery of other therapeutic agents, and when so used, will enhance the clinical response to such agents. Examples of these other therapeutic agents are: anti-inflammatory agents (e.g., corticosteroids, colchicine, sulfasalazine, and sulfones); antibiotics (e.g., quinolones, macrolides, penicillins, cephalosporins, sulfonamides, and tetracyclines); antivirals (e.g., acyclovir, idoxuridine, zidovudine, 2',3'-dideoxyinosine (ddI), vidarabine, and trifluridine); antifungals (e.g., ketoconazole, econazole, griseofulvin, cicloprix, and naftidine); antihistamines (e.g., diphenhydramine, astemizole, hydroxyzine, doxepin, amitriptyline, cyproheptadine, and sodium cromolyn); antipruritics (e.g., camphor, menthol, phenol, benzocaine, benzyl alcohol, salicylic acid, dyclonine, and pramoxine); antineoplastic agents (e.g., methotrexate, piritrexim, cisplatin, 5-fluorouracil, bleomycin, carmustine, hydroxyurea, azathioprine, and nitrogen mustard); carboxylic acid analogs (e.g., 1-monolaurin, azelaic acid and dodecanedioic acid); natural and synthetic vitamins and analogs (e.g., vitamin D, calcipitriol, 1,25-dihydroxy cholecalciferol, retinol, retinyl palmitate, retinyl ascorbate, isotretinoin, etretinate and retinoic acid); artemisinin analogs (e.g., artesunate, arteether, artemether, dihydroartemisinin and artelenic acid).

In addition to above agents, the composition of the present invention also comprises other ingredients commonly used in a cosmetic composition or a pharmaceutical composition. Examples of the other ingredients are: lipid ingredients, humectants, emollients, emulsifiers, organic or inorganic dyes, organic powders, ultraviolet ray absorbing agents, preservatives, antiseptics, antioxidants, plant extracts, pH controllers, alcohols, pigments, perfumes, blood circulators, refrigerants, antihidrotics, and distilled water.

The pseudolipid complex mixture comprising a pseudolipid and a stearic acid, and optionally a cholesterol has improved phase stability and a structure similar to that of the epidermal startum corneum which can retain a large amount of water and other beneficial materials. Accordingly, the composition comprising the complex mixture may be used as an external skin application composition through providing improved moisturization and barrier repair capabilities when applied to the skin. In particular, the composition may be used as cosmetic composition formulations such as oil-in-water emulsions or solubilized gels containing insoluble ceramides.

The following Examples are intended to illustrate the present invention without limiting its scope.

Examples 1, 2 and Comparative Examples 1, 2

The external skin application compositions of Example 1 and Comparative Example 2 were each formulated into an oil-in-water emulsion using the ingredients shown in Table 1, and the external skin application compositions of Example 2 and Comparative Example 2 were each formulated in the form of a gel using the ingredients shown in Table 2. In Examples 1 and 2, the pseudoceramide, cholesterol, and stearic acid were used in amounts of 40%, 20%, and 40% by weight (weight ratio 1:0.5:1), respectively, based on the total amount of the complex mixture.

TABLE 1

| | Ingredient (% by weight) | Example 1 | Example 2 |
|---|---|---|---|
| Oil phase ingredients | Stearic acid | 2.5 | 2.5 |
| | Cetearyl alcohol | 0.5 | 0.5 |
| | Glyceryl stearate/ PEG-100 stearate | 1.5 | 1.5 |
| | Cetyl octanoate | 4.0 | 4.0 |
| | Isopropyl palmitate | 4.0 | 4.0 |
| | 2-Octyl dodecanol | 4.0 | 4.0 |
| | Dimethicone | 1.0 | 1.0 |
| | Cyclomethicone | 3.0 | 3.0 |
| | Pseudolipid complex mixture (pseudoceramide (ceramide PC104):cholesterol:stearic acid = 1:0.5:1) | 2.0 | — |
| | Parahydroxybenzoate | A.A | A.A |
| Aqueous phase ingredients I | Distilled water | To 100 | To 100 |
| | Glycerin | 5.0 | 5.0 |
| | Butylene glycol | 5.0 | 5.0 |
| | Disodium EDTA | A.A | A.A |
| | TEAE | A.A | A.A |
| | Imidazolidinylurea | A.A | A.A |
| Aqueous phase ingredient II | 1% Cabomer solution | 12 | 12 |

A.A denotes "an appropriate amount"

<Method for Preparing the Compositions of Example 1 and Comparative Example 1>

(a) The oily ingredients were mixed and heated at 70 to 75° C. to obtain homogeneous mixture (i);

(b) The aqueous phase ingredients I were mixed and heated at 70 to 75° C. to obtain homogenous mixture (ii); and (c) Mixture (i) was added to the mixture (ii) while stirring at 70 to 75° C. to prepare an emulsion, and subsequently, the aqueous phase ingredient II was added thereto. The resulting mixture was cooled to 28 to 30° C. to obtain an oil-in-water emulsion.

TABLE 2

| | Ingredient (% by weight) | Example 2 | Comparative Example 2 |
|---|---|---|---|
| Aqueous phase ingredients 1 | Distilled water | To 100 | To 100 |
| | Glycerin | 5.0 | 5.0 |
| | Butylene glycol | 3.0 | 3.0 |
| | Disodium EDTA | A.A | A.A |
| | Trehalose | 1 | 1 |
| | Hyaluronic acid | 2 | 2 |
| | PEG-75 | 1 | 1 |
| | Potassium hydroxide | A.A | A.A |
| | Pseudolipid complex mixture (pseudoceramide (ceramide PC104):cholesterol:stearic acid = 1:0.5:1) | 0.1 | — |
| Aqueous phase ingredients II | 1% Cabomer solution | 20 | 20 |
| | Xanthan gum | 0.1 | 0.1 |
| Alcoholic ingredients | 95% ethanol | 5.0 | 5.0 |
| | Polyoxyethylene hydrogenated caster oil | 0.3 | 0.3 |
| | Parahydroxybenzoate | A.A | A.A |

A.A denotes "an appropriate amount"

<Method for Preparing the Compositions of Example 2 and Comparative

Example 2

(a) The aqueous phase ingredients I were mixed at 30° C. to obtain homogenous mixture (i);

(b) The alcoholic ingredients were mixed at 30° C. to obtain homogenous mixture (ii); and (c) The aqueous phase ingredients II were slowly added to mixture (i), and subsequently, mixture (ii) were added thereto, to obtain a gel formulation.

Experimental Example 1

Evaluation on Skin Barrier Repair Capabilities in Mice

The skin barrier repair capabilities of compositions of Examples 1, 2 and Comparative Examples 1, 2 were investigated as follows.

Hairless mice (Orient Bio. Inc., Korea), aged 8 to 10 weeks, were treated by repeated applications of acetone to the back, twice daily for total 5 days, to perturb the cutaneous barrier.

The rate of transepidermal water loss (TEWL) was then measured using an electrolytic water analyzer (delphin Co., Finland). As soon as the TEWL rates exceeded 40 g/m²/h, test formulations were applied topically to the barrier-perturbed areas. Each test formulation was applied twice daily for 3 days in an amount of 200 μL based on an area of 5 cm². Further measurements of TEWL were taken at a constant time interval, and the results were shown in FIG. 6.

Figure 6:
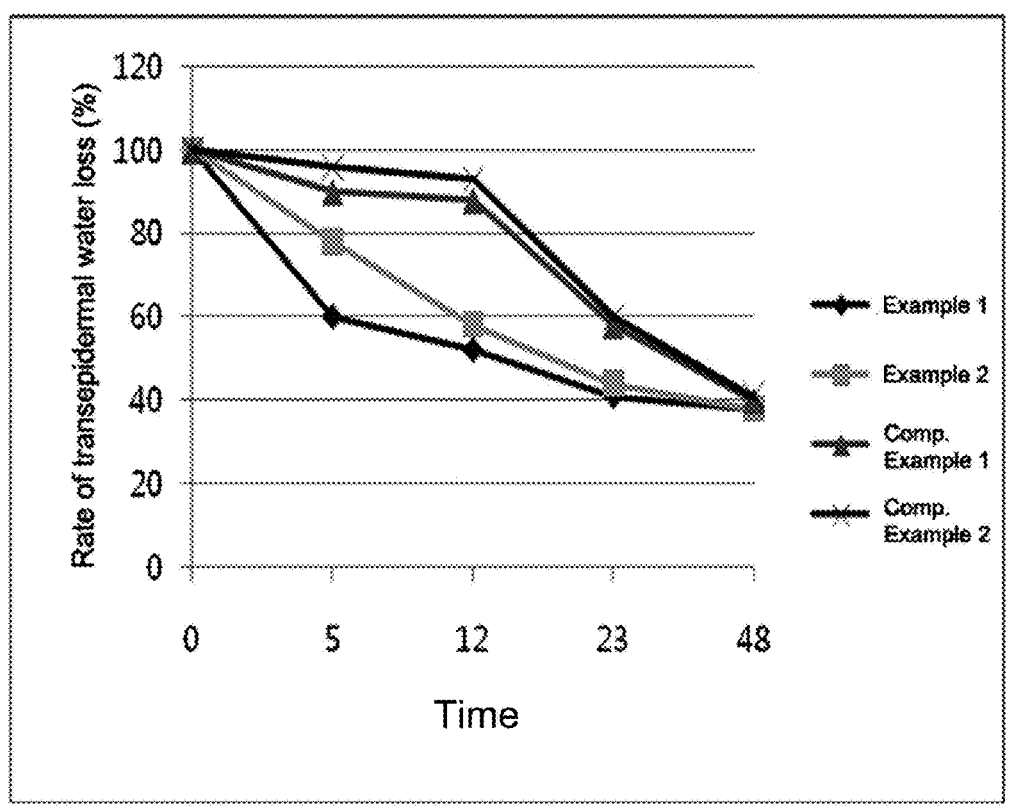
FIG. 6: Changes in the trans-epidermal water loss in mice having its skin barrier function disrupted when treated with the external skin application composition of the present invention.

As shown in FIG. 6, the groups treated with the compositions of Examples 1 and 2 exhibited a fast barrier repair capabilities, as compared with the groups treated with the compositions of Comparative Examples 1 and 2. In particular, the rate of transepidermal water loss measured at 12 hours after disruption of barrier function was about 40% when applied with the compositions of Examples 1 and 2, which demonstrates remarkable barrier repair capabilities of the inventive compositions.

Experimental Example 2

Evaluation on Moisturization in Human

The moisturization effect of oil-in-water emulsions and solubilized gels prepared in above Examples 1, 2 and Comparative Examples 1, 2 was tested as follows:

(a) Water Content

Forty male and female adults aged fifties to sixties, in four groups of ten each, were treated twice daily for 4 weeks by applying to their faces with the cosmetic composition of Examples 1, 2 and Comparative Examples 1, 2. Skin conductance was measured prior to application of the compositions, and again at 1 week, 2 weeks, 4 weeks after application of the composition, and at 2 weeks after 4-week application stops (6 weeks after application), under 24° C. and 40% relative humidity by using corneometer for the measurement of water content of the skin. The results of Table 3 show an increase in the water content after application of the compositions.

TABLE 3

| | Increase of water content (%) | | | |
|---|---|---|---|---|
| | 1 week after application | 2 weeks after application | 3 weeks after application | 2 weeks after 4-week application stops (6 weeks after application) |
| Example 1 | 41 | 48 | 51 | 45 |
| Example 2 | 31 | 34 | 39 | 36 |
| Comparative Example 1 | 35 | 37 | 42 | 28 |
| Comparative Example 2 | 27 | 31 | 33 | 16 |

As shown in Table 3, the water contents of the groups treated with the compositions of Examples 1 and 2 were higher than those of the groups treated with the composition of Comparative Examples 1 and 2. Further, the water contents measured at 2 weeks after 4-week application stops (6 weeks after application) were similar to those measured after 1 or 2 weeks. The results indicate that the inventive composition can retain water persistently, even after application stops.

(b) Subjective Evaluation

As soon as above experiment (a) terminated, the effects of the inventive compositions were evaluated in subjective manners. The results were shown in Table 4.

TABLE 4

| | Result of questions survey (person) | | | |
|---|---|---|---|---|
| | Very good | Good | Average | Poor |
| Example 1 | 2 | 9 | 1 | 0 |
| Example 2 | 1 | 5 | 3 | 0 |
| Comparative Example 3 | 2 | 6 | 1 | 1 |
| Comparative Example 4 | 0 | 4 | 4 | 1 |

As shown in Table 4, the compositions of Examples 1 and 2 ameliorated the dryness of the skin.

While the invention has been described with respect to the above specific embodiments, it should be recognized that various modifications and changes may be made and also fall within the scope of the invention as defined by the claims that follow.

What is claimed is:

1. A pseudolipid complex mixture composition consisting of a pseudoceramide represented by formula (II), a stearic acid, and cholesterol,

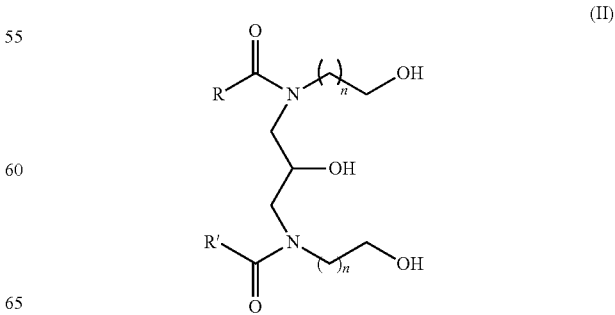

(II)

wherein n is 1 or 2; and

R and R' are each a saturated or unsaturated $C_9$-$C_{21}$ aliphatic chain moiety, wherein the amounts of the pseudoceramide, cholesterol and stearic acid are 10 to 80% by weight, 0.0001 to 30% by weight and 10 to 80% by weight, respectively, based on the total amount of the complex mixture.

2. The composition of claim 1, wherein the composition is a cosmetic composition or a pharmaceutical composition.

* * * * *